(12) United States Patent
Kaw et al.

(10) Patent No.: US 7,758,884 B2
(45) Date of Patent: Jul. 20, 2010

(54) FORMULATION FOR INCREASING THE DEPOSITION OF DIETARY CAROTENOIDS IN EGGS

(75) Inventors: Leow Sai Kaw, Johor (MY); Goh Swee Keng, Singapore (SG); Jesuadimai Ignatius Xavier Antony, Singapore (SG); Hai Meng Tan, Singapore (SG)

(73) Assignee: Kemin Industries, Inc., Des Moines, IA (US)

( * ) Notice: Subject to any disclaimer, the term of this patent is extended or adjusted under 35 U.S.C. 154(b) by 1027 days.

(21) Appl. No.: 11/045,522

(22) Filed: Jan. 28, 2005

(65) Prior Publication Data

US 2006/0171995 A1   Aug. 3, 2006

(51) Int. Cl.
*A23K 1/17* (2006.01)
*A61K 9/50* (2006.01)
*A61K 36/899* (2006.01)
*A61K 36/31* (2006.01)
*A61K 36/889* (2006.01)
*A61K 36/48* (2006.01)
*A61K 36/28* (2006.01)
*A61K 31/015* (2006.01)
*A01N 35/00* (2006.01)

(52) U.S. Cl. ............... 424/442; 424/502; 424/750; 424/755; 424/727; 424/757; 424/764; 514/763; 514/690

(58) Field of Classification Search .......... 426/2, 426/540; 424/442, 502, 750, 755, 727, 757, 424/764; 514/763, 690
See application file for complete search history.

(56) References Cited

U.S. PATENT DOCUMENTS 3,539,686 A * 11/1970 Rosenberg ............... 424/760

(Continued)

FOREIGN PATENT DOCUMENTS

AU    745973    12/1999

(Continued)

OTHER PUBLICATIONS

Philip, T., Weber, C.W., Berry, J.W., "Utilization of Lutein and Lutein-Fatty Acid Esters by Laying hens", Journal of food Science, 41(1), 23-25, 1976.

(Continued)

*Primary Examiner*—Robert A Wax
*Assistant Examiner*—Aradhana Sasan
(74) *Attorney, Agent, or Firm*—Kent A. Herink; Emily E. Harris

(57) ABSTRACT

The absorption and deposition of carotenoids added to poultry diets into the yolk of eggs produced by the poultry is improved by adding a carotenoid formulation comprising a carotenoid, a vegetable oil, a surfactant, a chelating agent, an antioxidant, an alkali and a solvent. The carotenoid formulation can reduce the crystalline nature of lutein for its better dissolution in the formulation and the diet. This new formulation is capable of making more micelles for an effective transfer of lutein from the formulations to the aqueous layer. The new formulation can increase the bioavailability of lutein in chicken biological system and leads to more deposition in the blood and the egg. The lutein deposition in the egg was consistent for an extended period of time when this new formulation was added to the diet. Addition of this carotenoid formulation to the diet increased the antioxidant power of the blood. Eggs produced by poultry fed diets supplemented by the formulation have in excess of 0.80 mg carotenoids per 100 grams of edible portion and thus serve as an important source of carotenoids in the human diet.

17 Claims, 4 Drawing Sheets

Carotenoid formulation with crystalline lutein

New carotenoid formulation with reduced crystalline lutein

U.S. PATENT DOCUMENTS

| | | | |
|---|---|---|---|
| 4,316,917 A * | 2/1982 | Antoshkiw et al. | 426/540 |
| 4,877,635 A * | 10/1989 | Todd, Jr. | 426/542 |
| 5,607,707 A * | 3/1997 | Ford et al. | 426/2 |
| 5,648,564 A * | 7/1997 | Ausich et al. | 568/834 |
| 5,670,548 A * | 9/1997 | Bernhard et al. | 514/725 |
| 5,863,953 A * | 1/1999 | Luddecke et al. | 514/691 |
| 6,075,058 A | 6/2000 | Handelman | |
| 6,156,351 A | 12/2000 | Shapira | |
| 6,235,315 B1 | 5/2001 | Auweter et al. | |
| 6,248,363 B1 | 6/2001 | Patel et al. | |
| 6,287,615 B1 | 9/2001 | Zwissler et al. | |
| 6,376,722 B1 * | 4/2002 | Sanz et al. | 568/816 |
| 6,426,069 B1 | 7/2002 | Yesair | |
| 6,509,029 B2 | 1/2003 | Runge et al. | |
| 2004/0022881 A1 * | 2/2004 | Hauptmann et al. | 424/764 |

FOREIGN PATENT DOCUMENTS

| | | |
|---|---|---|
| JP | 06197703 | 7/1994 |
| JP | 2003-102395 | 4/2003 |

OTHER PUBLICATIONS

Hamilton, P.B., Parkhurst, C.R. "Imporived depostiion of oxycarotenoids in egg yolks by dietary cottonseed oil", Poultry Science, 69, 354-359, 1989.

Bowen, P.E., Herbst-Espinosa, S.M., Hussain, E.A., Stacewicz-Sapuntzakis, M., "Esterification does not impair lutein bioavailability in humans", Journal of Nutrition, 132, 3668-3673, 2002.

Idit, A., Abraham, A., Nissim, G., "Solibiliztion patterns of lutein and lutein esters in food grade nonionic microemulsions", Journal of Agriculture and Food Chemistry, 51, 4775-4781, 2003.

Seteve, L., "Lutein enriched eggs, transfer of lutein into eggs and health benefits", 2004.

Troche, C., Katti, S., Novak, C., Ruszler, P., Sanders, D., "The effect of lutein complex on yolk color, yolk content and other production parameters in laying hens".

* cited by examiner

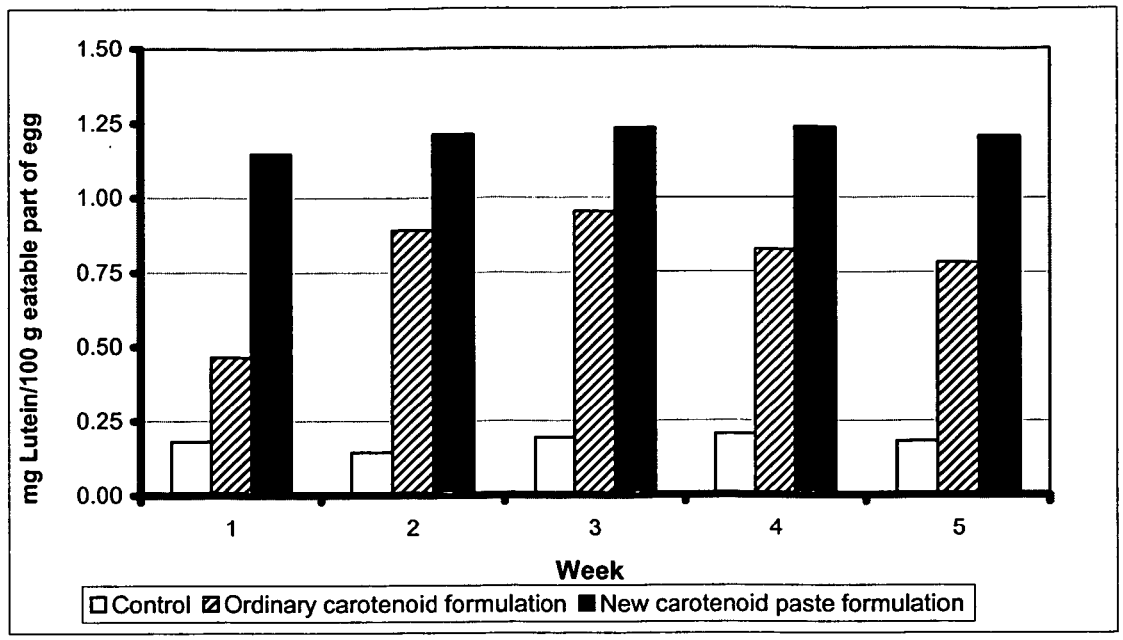
FIG. 5
Figure 6
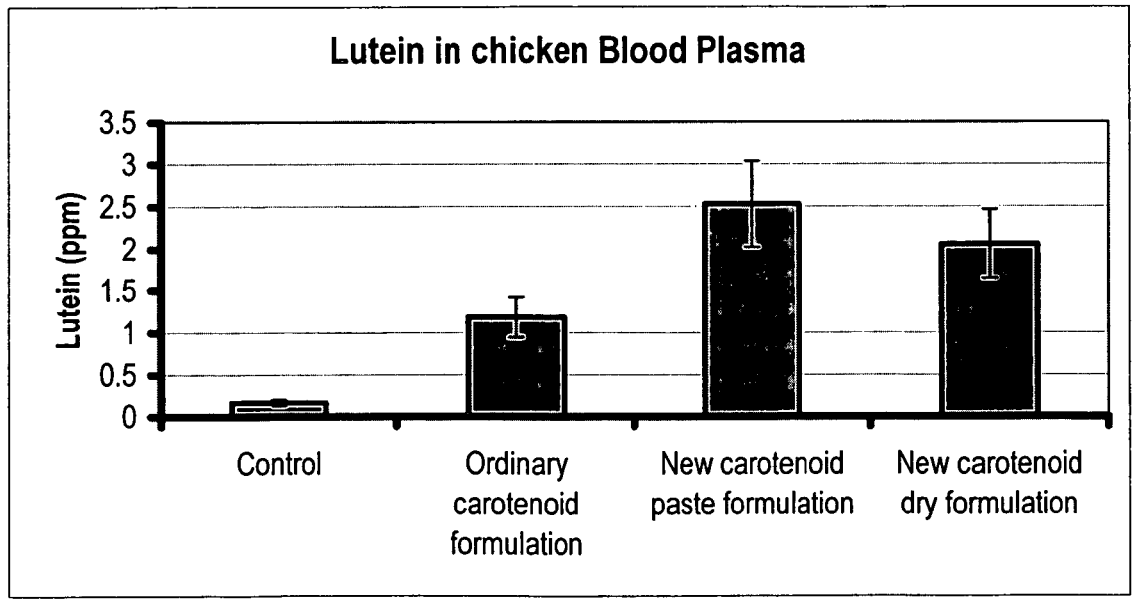
FIG. 6

US 7,758,884 B2

FORMULATION FOR INCREASING THE DEPOSITION OF DIETARY CAROTENOIDS IN EGGS

BACKGROUND OF THE INVENTION

The invention relates generally to the addition of carotenoids to layer chicken diets and, more specifically, to a formulation of carotenoids combined with a vegetable oil, a surfactant, a chelating agent, an antioxidant, an alkali and a solvent to improve the amount of carotenoids deposited in the yolk of eggs and other parts of the chickens.

Consumers have started to view food from a functional viewpoint. Functional foods can be defined as those providing health benefits beyond basic nutrition. Interest in functional foods increased in the last decade due to the overwhelming scientific evidence highlighting the relation between diet and health. The interest in functional foods has resulted in a number of new foods in the marketplace designed to address specific health concerns, particularly as regards chronic diseases of aging. In addition to new functional foods traditional foods and familiar foods are also found to have potential health benefits. A classic example is eggs. Eggs have not traditionally been regarded as a functional food, primarily due to concerns about their adverse effects on serum cholesterol levels. It is now known that consuming one egg per day does not adversely increase the blood cholesterol levels. Finally, eggs are increasingly being seen as a dietary source of essential components, including carotenoids and in particular the carotenoid lutein.

Carotenoids are fat-soluble compounds and their absorption involves solubilization and incorporation into micelles. In humans at least, the actual intestinal uptake is believed to occur by passive diffusion along with uptake of dietary fat. The presence of dietary fat is thought to be important for micelle formation in the small intestine; dietary fat therefore, may also be crucial for absorption of carotenoids. The addition of fat has been reported to increase the bioavailability of lutein. Lutein is a well-reported phytonutrient for eye health. Lutein is an oxy-carotenoid present in many plants and dark leafy vegetables such as spinach and kale. Purified crystalline lutein has a bright orange-yellow color. Lutein intake has been reported to be declining in the United States to between 1.5 and 2 mg/day, attributed primarily to the decrease in the consumption of dark greens. Egg yolk contains lutein but in very low concentration (approximately 0.1 mg/100 g edible part of egg). Eggs could be a source of lutein if the lutein content is increased to 1 mg/100 g edible part.

Accordingly, there is a need for an animal feed ingredient formulation that will improve the deposition of carotenoids in the yolk of eggs of birds fed the formulation. Eggs with an increased level of carotenoids will provide higher levels of the needed carotenoids to humans who eat the eggs.

SUMMARY OF THE INVENTION

The invention consists of formulations of carotenoids that improve the absorption and deposition of the carotenoids into egg yolks and other parts of the birds fed a diet supplemented with the formulations. The formulations consist of a bioavailable source of carotenoids combined with a vegetable oil, a surfactant, a chelating agent, an antioxidant, an alkali and a solvent. The formulations are made by saponifying the plant extracts containing carotenoid ester and emulsifying it with a vegetable oil using a surfactant. Preferably, the formulations are added to poultry diets between about 0.01 wt % and 0.5 wt % and most preferably between about 0.2 wt % and about 0.3 wt %. Eggs produced by poultry fed a diet supplemented with the formulations contain in excess of 1.0 mg carotenoids per 100 g of edible portion of the egg.

BRIEF DESCRIPTION OF THE FIGURES

FIG. 5 is a graph showing the effect of new formulation on the consistency of lutein deposition in egg.

FIG. 6 is a graph showing the effect of new formulation and the new formulation in dry form on the lutein deposition in chicken blood plasma.

DETAILED DESCRIPTION OF PREFERRED EMBODIMENTS

Saponification is a chemical process employed to cleavage an ester into its corresponding alcohol and the acid. Carotenoids are present in ester form in the natural sources. In this new formulation the saponification process is used to free the carotenoids from their esters. A suitable alkali and a solvent are used for the saponification process.

Carotenoids are sensitive to oxidation. Presences of trace metals induce the non-reversible oxidation process. A chelating agent is added in the new formulation to chelate the trace metals in the feed to help protect the carotenoids from the damage of oxidation. In addition an antioxidant is also added in the new formulation to help protect the carotenoids from the oxidation process. Carotenoids preferred for use in the new formulation include lutein, zeaxanthin, beta-carotene, trans-capsanthin, capsorubin and the carotenoid derivatives from lycopene.

Figures 1A, 1B:
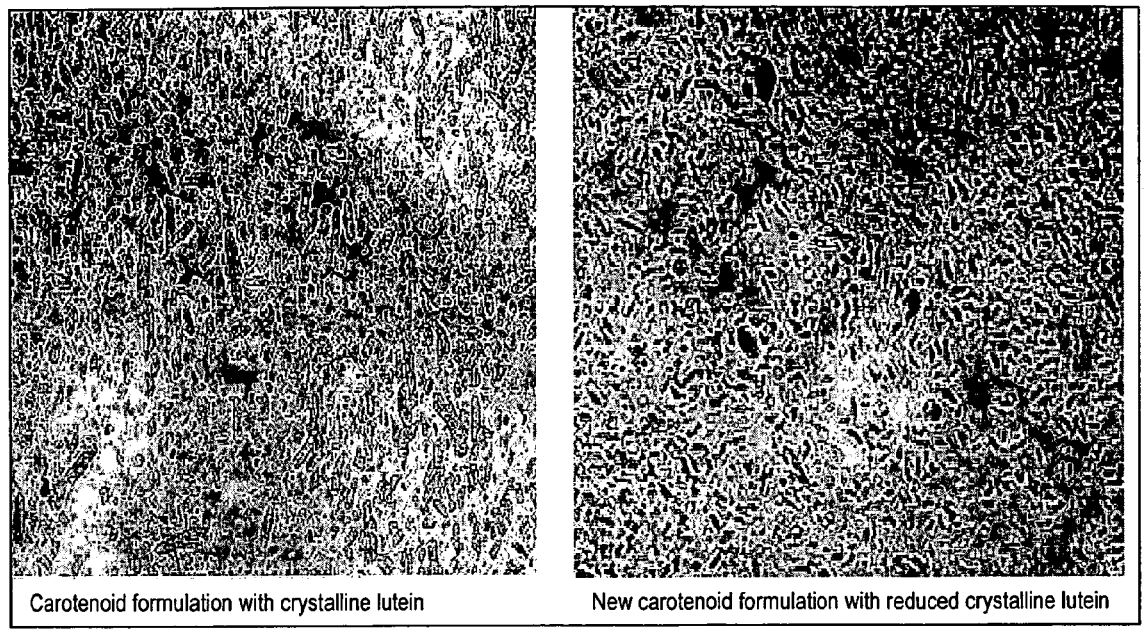
FIGS. 1a and 1b are photomicrographs of a lutein paste formulation without vegetable oil and surfactant and the new emulsified formulation with added vegetable oil and surfactant; respectively, showing the reduced size of the crystals of lutein in the new emulsified formulation.

Fat from animal sources and vegetable sources is added to the poultry diets as a source of energy to increase egg production, reduce dust from feed rations, enhance palatability, and provide a source of essential fatty acids. In this new formulation a vegetable oil is used to reduce the crystalline nature of lutein and increase its dissolution in the formulation. FIGS. 1a and 1b show the normal formulation containing crystalline lutein and the new improved emulsified formulation made with the same crystalline lutein product wherein the new formulation has lutein crystals of a reduced size.

Surfactants are surface-active agents used in formulations to disperse two immiscible phases with each other to form an emulsion. An emulsified formulation is expected to enhance the micelle formation in the digestive system. Lutein is transported into the blood by micelles. Therefore, the new emulsified formulation is capable of transporting lutein from the feed matrix into the chicken biological system more effectively.

A preferred carotenoid source suitable for use in poultry feeds comprises yellow, orange and/or red xanthophylls. The non-emulsified or control carotenoid source used in the examples is a stabilized source of saponified yellow carotenoids from marigolds for use in poultry feeds and is available from Kemin Agrifoods Asia. (Singapore) under the product name Oro GLO 20 Dry.

The novel carotenoid formulations of the present invention used in the examples are prepared from the marigold oleoresin in either in paste form or in dry form. The new paste formulation is prepared by adding to a reaction vessel a suitable solvent, the xanthophyll source, an antioxidant and a chelating agent and stirring or mixing to form a substantially homogenous mixture. An alkali solution is added under stirring and the mixture is incubated at an elevated temperature until the saponification reaction is complete. A mixture of vegetable oil and surfactant is added to the saponified mixture. The amount of the vegetable oil and surfactant are adjusted to form an emulsification. To prepare an alternative preferred embodiment in dry form the paste form is added to a sufficient amount of a dry carrier while stirring to form a dry, flowing product.

Vegetable oils preferred for use in the formulations of the present invention include corn oil, rapeseed oil, soybean oil, palm oil, sunflower oil and coconut oil. The vegetable oil comprises between about 1 weight % and about 90 weight % of the formulation, and preferably between about 40 weight % and about 50 weight %, and most preferably between about 42.857 weight % and about 47.369 weight %. Surfactants preferred for use in the formulations of the present invention include surfactants having an HLB number between about 1 and about 12 and preferably between about 3 and 6. Specific preferred surfactants include sorbitan fatty acid esters. The surfactants are added to the formulation in an amount between about 0.001 weight % and about 10 weight %, and preferably between about 1 weight % and about 3 weight %, and most preferably between about 2.375 weight % and about 2.625 weight %. Chelating agents preferred for use in the formulations of the present invention include EDTA and citric acid. The chelating agents are added to the formulation in an amount between about 0.001 weight % and about 1 weight %, and preferably between about 0.01 weight % and about 0.2 weight %, and most preferably between about 0.03 weight % and about 0.07 weight %. Antioxidants preferred for use in the formulations of the present invention include ethoxyquin, butylated hydroxy anisole, butylated hydroxy toluene, propyl gallate, octyl gallate, gallic acid, catechins, polyphenols, tocopherols, rosemary extract and curcuminoids. The antioxidants are added to the formulation in an amount between about 0.1 weight % and about 10 weight %, and preferably between about 0.2 weight % and about 5 weight %, and most preferably between about 0.4 weight % and about 3 weight %. Solvents preferred for use in the formulations of the present invention include alcohols, and specifically propylene glycol and benzyl alcohol. The solvents are added to the formulation in an amount between about 1 weight % and about 40 weight %, and preferably between about 10 weight % and about 35 weight %, and most preferably between about 15 weight % and about 32 weight %. Alkaline compounds preferred for use in the formulations of the present invention include aqueous solutions of potassium hydroxide and sodium hydroxide. The alkaline compounds are added to the formulation in an amount between about 1 weight % and about 20 weight %, and preferably between about 1 weight % and about 10 weight %, and most preferably between about 2 weight % and about 6 weight %. If a dry form of the product is desired, an inert carrier is used. Inert carriers preferred for use in the formulations of the present invention include rice bran, wheat bran, silica, bentonite, calcium carbonate and vermiculite.

A preferred embodiment of the new paste formulation of the present invention was made according to the following method. To a reaction vessel, 25.878 wt % propylene glycol was added. Ethoxyquin (1.95 wt %), a 1:3 EDTA:water (0.4 wt %) solution, and marigold oleoresin (50.167 wt %) were added. An agitator was started and ran for a sufficient time to ensure complete mixing. A 45% aqueous potassium hydroxide solution (21.605 wt %) was added. The vessel was maintained at between 56 and 60° for a minimum of 2.5 hours or until the saponification reaction is complete. Because the xanthophyll content of the marigold oleoresin varies from between about 90 g/kg and about 150 g/kg, the amount of the saponified mixture for use in the next stage of the method is selected to ensure that the carotenoid level will match that required for the product. Accordingly, the amount of the saponified mixture in the next stage for a specified level of 20.5 g/kg carotenoids will vary between 27.244 and 45.407 wt %. The temperature of the saponified mixture is maintained at between 56 and 600. Between 42.857 and 47.369 wt % corn oil is added to a different reaction vessel under agitation or stirring and between 2.375 and 2.625 wt % Span 80® (ICI Americas, Wilmington, Del.) a sufficient wt % of propylene glycol to total 100 wt % are added to the oil. The appropriate amount of the saponified mixture is then added and stirring is continued to ensure a homogeneous mixture.

To form a preferred embodiment of a dry formulation of the present invention having a carotenoid content of 13.5 g/kg, 65.854 wt % of the paste formulation is added to 34.146 wt % silica and the mixture is stirred until a uniform color results.

The paste product of the preferred embodiment contains 15 grams of lutein activity per kilogram and the preferred dry formulation contains 10 grams of lutein activity per kilogram. Table 1 shows the details of the formulations used in the examples.

TABLE 1

Composition of the formulations used in the examples

| Ingredients | Ordinary Formulation | New Paste Formulation | New Dry Formulation |
|---|---|---|---|
| Xanthophylls g/kg | 20 | 20 | 13.5 |
| Lutein g/kg | 15 | 15 | 10 |
| Chelating agent | Present | Present | Present |
| Vegetable oil % | Nil | 46 | 30 |
| Surfactant % | Nil | 2.5 | 2.5 |
| Antioxidant % | Present | Present | Present |
| Organic dry carrier % | 35 | Nil | Nil |
| Dry carrier % | 23 | Nil | 39 |

EXAMPLE 1

Materials and Methods

All solvents and reagents used in the current study were of Analar Reagent grade. An in vitro method was employed to measure the micellarized lutein in the aqueous layer. This in vitro protocol was simulating the four stages of the chicken's digestive system namely crop, proventriculus, gizzard and small intestine. The pigment formulation sample was taken, mixed with saline and the pH of the mixture was adjusted to 5.5. This mixture was incubated for 30 minutes at 41° C. Pepsin solution was added to the incubated mixture and the pH was adjusted to 4 before subjecting this mixture to one hour incubation at 41° C. The pH of the incubated mixture was adjusted to 5.3 and pancreatic juice was added. The pH of this mixture was then raised to 7 and subjected to one-hour incubation at 41° C. This digested mixture was centrifuged and the aqueous layer containing the micelles was carefully separated for lutein quantification. The ordinary and the new paste carotenoid formulations were subjected to this protocol and the micellarized lutein that was transferred to the aqueous layer from these formulations was measured. For each formulation four experiments were done and the average values are reported in FIG. 2. The % bioavailability of the lutein from these formulations was calculated from the initial lutein content of the formulations.

Results and Discussion

Figure 2:
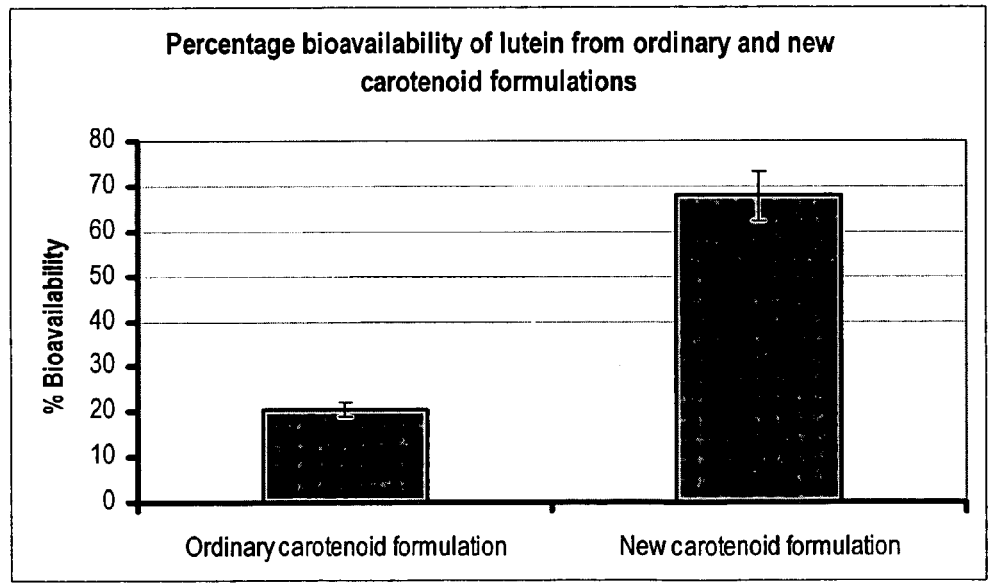
FIG. 2 is a graph showing the effect of the new formulation on the concentration of the micellarized lutein in an aqueous layer.

FIG. 2 shows the results from this in vitro study. It was found the new paste formulation showed a 67.84% bioavailability for lutein and the ordinary formulation showed 20.43% bioavailability for lutein. From this study it is evident that the new improved emulsified formulation could make more effective micelles and transported more lutein into the aqueous layer.

EXAMPLE 2

Materials and Methods

All solvents and reagents used in the current study were of Analar Reagent grade. Analytical lutein was procured from Kemin Food (Des Moines, Iowa).

Experimental Details

A trial was conducted using a control and two different treatments. Table 2 gives the composition of the control diet used in this trial. The treatments were designed to study the effect of the new emulsified paste formulation over and non-emulsified ordinary formulation on the lutein deposition in egg and in chicken blood. The first treatment was a control where none of the above ingredients were added. Treatments 2 and 3 were the experimental formulations. These experimental carotenoid formulations were added at a rate of 2 kg per metric ton of chicken feed. The lutein content in the mixed feed was approximately 30 g per metric ton of feed. Twenty-two week old Lohamann Brown hens were used. The birds were fed with the experimental diets and allowed two weeks for adaptation to their new environment. The hens were placed in individual wire-floored cages arranged in two tires within an open-sided house. The birds were under 14L; 10 D lighting regime. Four cages of birds were fed from a single feed trough and considered as an experimental replicate and each experimental diet were to five replicates (20 birds per treatment). Feed and water were provided ad libitum throughout the experimental diet. Each week, ten eggs from each dietary group were taken for lutein analysis. On the third week and fifth week six birds per dietary group were randomly chosen and blood samples were collected. The plasma was separated from blood and the lutein content was quantified. Data were statistically analyzed by one-way ANOVA method.

TABLE 2

Composition of the control diet

| | Percentage (%) |
|---|---|
| Ingredients | |
| Corn | 58.46 |
| Soybean meal | 28.30 |
| Fishmeal | 1.00 |
| Palm oil | 1.15 |
| Limestone | 9.10 |
| Dicalcium phosphate | 1.50 |
| Antioxidant | 0.01 |
| Salt | 0.16 |
| Vitamin-mineral premix | 0.10 |
| DL-methionine | 0.12 |
| Choline chloride | 0.1 |
| Calculated composition | |
| Nutrients | |
| AME, kcal/kg | 2691 |
| Crude protein | 18.20% |
| Crude fat | 3.68% |
| Crude fiber | 3.05% |
| Calcium | 3.96% |
| Available phosphorous | 0.45% |
| Lysine | 1.04% |
| Methionine | 0.38% |

HPLC Analysis

All lutein analyses were done in duplicate and the average value was calculated. For each analysis egg yolks and the whites from two to three eggs were taken. These yolks and whites were pooled together, mixed thoroughly and sampled for analysis. A 1.0 g sample was weighed into a 100 ml volumetric flask. One ml de-ionized water and 30 ml extracting solvent (hexane:ethanol:acetone:toluene 10:6:7:7 v/v) were added into the flask. The contents were ultra-sonicated for 2 minutes, and 6 ml 40% methanolic potassium hydroxide was added into the flask. The mixture was subjected to heating in a water bath at 56° C. for 30 minutes. The saponified mixture was transferred to a 250 ml separating funnel, and 30 ml extracting solvent and 40 ml 3% sodium sulfate solution were added. The layers were mixed gently to extract the pigments to the organic layer. The aqueous layer was drained into another separating funnel and washed with 30 ml extracting solvent. The lower aqueous layer was discarded and the organic layer was separated. The organic layers were pooled together and washed 4 times with 50 ml de-ionized water. The organic layer was evaporated to dryness under vacuum. The residue was dissolved in 10 ml HPLC mobile phase (hexane:acetone 81:19 v/v)

The xanthophylls separation was done using a normal phase HPLC method. The HPLC used was Agilent Technologies 1100 series. The column was a Shimadzu CLC-SIL (M) 150 mm×4.6 mm, PDA detector was set at 450 nm, and mobile phase was hexane:acetone 81:19 mixture with a flow rate of 1.1 ml/min. The column temperature was maintained at 30° C. For each analysis 20 µl of sample was injected into the HPLC using an auto-sampler. The lutein peak was identified using a lutein solution made from analytical grade lutein as standard. The amount of lutein in egg was quantified using an absolute calibration method.

Results and Discussion

Figure 3:
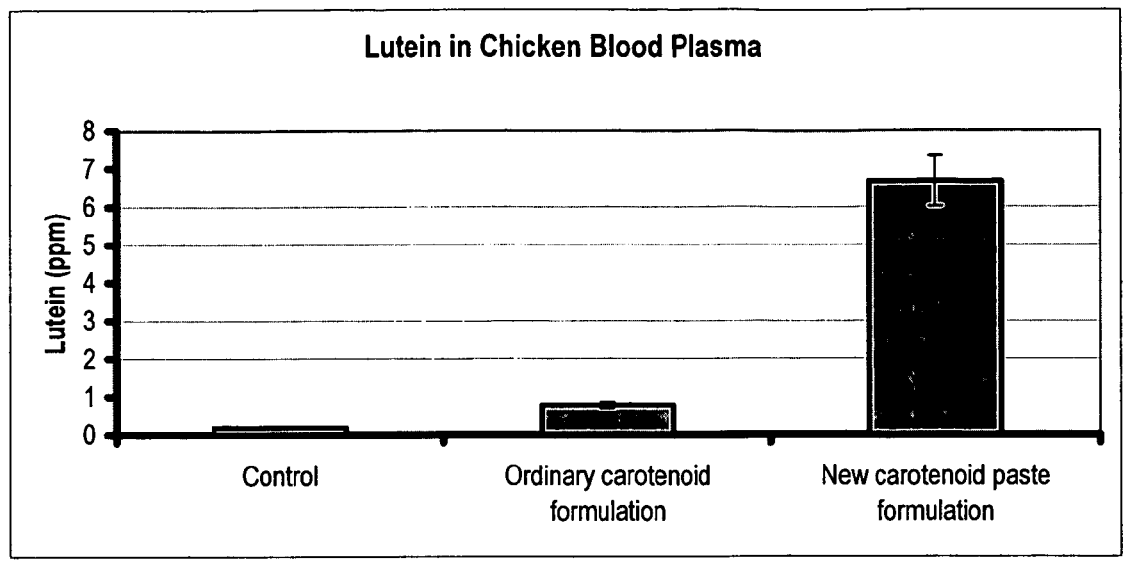
FIG. 3 is a graph showing the effect of new formulation on the lutein content in chicken blood plasma.

FIG. 3 shows the average results on the lutein deposition in the chicken blood plasma for the three treatments collected on week 3 and 5. The results indicate that the lutein deposition in the blood plasma was significantly higher for the birds fed with diet with the new carotenoids formulation than the ordinary formulation. The blood plasma collected from the birds treated with the new carotenoid formulation showed an average value of 6.67 ppm of lutein and the samples taken from the birds treated with the control diet and the ordinary carotenoid formulation showed average values of 0.18 ppm and 0.78 ppm respectively.

Figure 4:
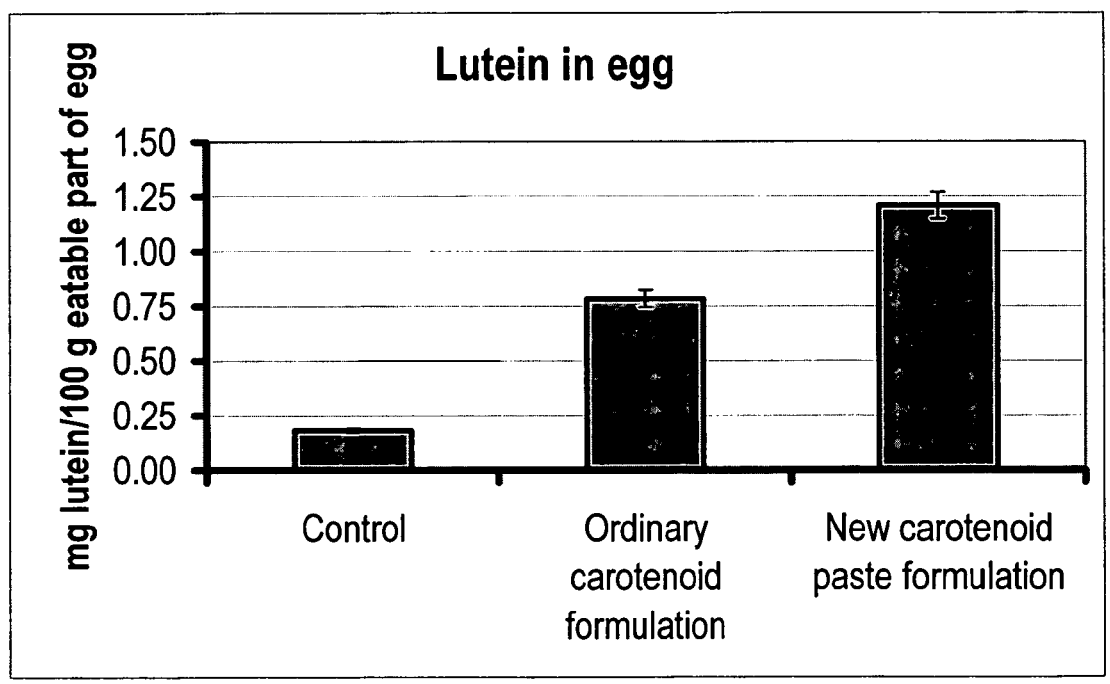
FIG. 4 is a graph showing the effect of new formulation on the lutein deposition in egg.

FIG. 4 shows the average four weeks results on the lutein deposition in the egg. The results indicate that the eggs collected from the birds treated with the new carotenoid paste formulation showed 1.21 mg lutein deposition per 100 of edible part of the egg. The eggs collected from the control treatment and the ordinary carotenoids formulation treatment showed 0.18 mg and 0.78 mg lutein per 100 gram edible part of the egg, respectively. From these results it can be seen that there is a 54% increase in the lutein deposition from the new formulation over the ordinary formulation. It is also important to note that there is a 6.7 fold increase in the lutein deposition in the egg from the new formulation over the eggs collected from the birds treated with the control diet.

FIG. 5 shows the effect of the new carotenoid formulation on the consistent lutein deposition in the egg over a period of four weeks. The results indicate that the performance of the new formulation is consistent. The lutein deposition in the eggs collected form this treatment was between 1.14 and 1.24 mg lutein per 100 gram edible part of the egg. The lutein deposition in the eggs collected from the birds treated with the ordinary formulation showed an initial increase in the lutein deposition in the second week and thereafter the lutein deposition showed a decreasing trend.

It was the objective of the present study to maximize the deposition of lutein in egg yolk. From the present trial, it was found that the untreated eggs contain about 0.18 mg lutein per 100 g edible part. In this present study efforts were made to boost the lutein content to more than 1 mg/100 g edible part of egg by using the carotenoid source as the main source of xanthophylls (lutein) in the feed. Earlier studies have shown the pigmenting efficacy of the carotenoid source In addition, the effects of addition of the carotenoid source with vegetable oil and surfactant on enhancing the bioavailability of lutein were also studied.

The results from this study showed that the lutein bioavailability from the new carotenoid formulation was significantly higher than the ordinary carotenoid formulation. The lutein deposition in the blood plasma taken from the birds treated with the new carotenoid formulation was 6.67 ppm. The plasma samples taken from the birds treated with the control diet and the ordinary carotenoid formulation showed average values of 0.18 ppm and 0.78 ppm respectively.

Conclusion

From the present study it may be concluded that addition of the new carotenoid paste formulation significantly increased the lutein content in the chicken blood plasma and egg. The eggs collected from the birds treated with the new formulation showed an average deposition of 1.21 mg lutein per 100 gram edible part of the egg. The eggs from the birds treated with control diet and the ordinary carotenoid formulation showed an average lutein deposition of 0.18 mg and 0.78 mg lutein per 100 gram edible part of egg. The new formulation gives a consistent lutein deposition in the egg.

EXAMPLE 3

Materials and Methods

A trial was conducted to study the effect of the new carotenoid formulation in the dry form. The new carotenoid paste formulation and the ordinary carotenoids formulation were also subjected to this trial. The trial included a control and three different treatments. All solvents were from Merck (Germany). Analytical lutein was procured from Kemin Foods, L.C. (Des Moines, Iowa).

Experimental Details

A trial was conducted using a control and three different treatments. The same control diet composition used in Example 1 (Table 2) was used in this trial. The ordinary carotenoid formulation and the new carotenoid paste formulation were included at rate of 2 kilogram per metric ton of feed. The inclusion rate of the new carotenoid dry formulation was 3 kilogram per metric ton of feed. For all the three experimental treatments the concentration of lutein in the feed was approximately 30 gram per metric ton. Twenty two weeks old Lohamann Brown hens were used. The birds were fed with the experimental diets and allowed one week for adaptation to their new environment. The hens were placed in individual wire-floored cages arranged in two tires within an open-sided house. The birds were under 14 L; 10 D lighting regime. Four cages of birds were fed from a single feed trough and considered as an experimental replicate and each experimental diet were to eight replicates (32 birds per treatment). Feed and water were provided ad libitum throughout the experimental diet. Each week, ten eggs from each dietary group were taken for lutein analysis. On the third week and fifth week six birds per dietary group were randomly chosen and blood samples were collected. The plasma was separated from blood and the lutein content was quantified. Data were statistically analyzed by one-way ANOVA method.

Results and Discussion

FIG. 6 shows the effect of the new carotenoid formulation in paste and dry forms. The lutein concentration in the plasma was higher for the sample drawn from the birds treated with both the new formulation. The lutein content in the blood plasma drawn for the birds treated with the control diet, ordinary carotenoid formulation, new carotenoid paste formulation and new carotenoid dry formulation was 0.17, 1.18, 2.53 and 2.06 ppm respectively. The results showed that both the new formulation showed significantly higher lutein deposition in the blood plasma than the control diet and the ordinary carotenoid formulation.

Figure 7:
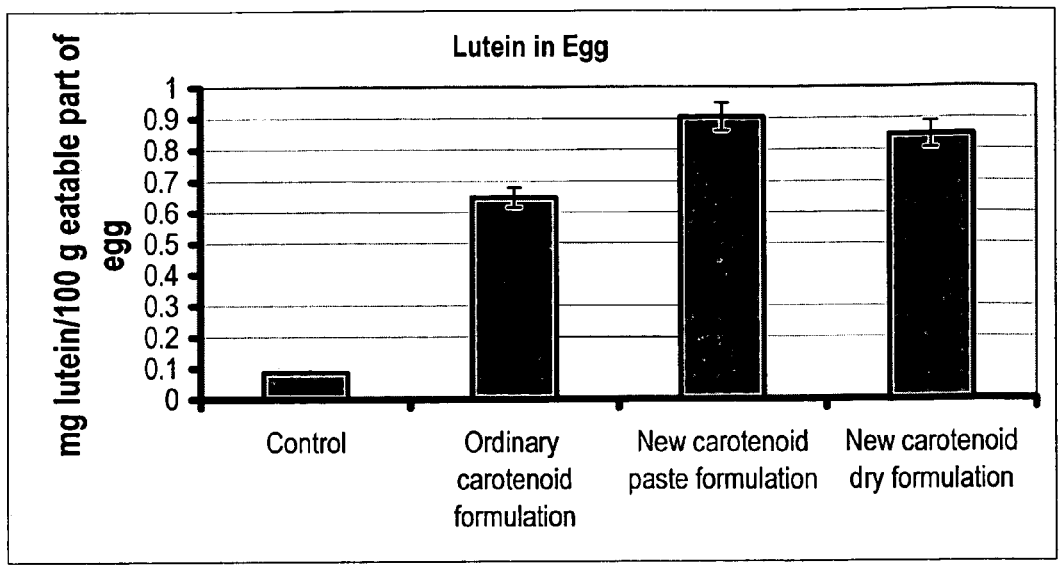
FIG. 7 is a graph showing the effect of new formulation and the new formulation in dry form on the lutein deposition in chicken egg.

FIG. 7 shows the average four weeks results on the lutein deposition in the egg. The results indicate that the eggs collected from the birds treated with both new carotenoid formulations showed significantly higher lutein content than the eggs collected from the birds treated control diet and ordinary carotenoid formulation. The lutein content in the eggs collected from the birds treated with the new carotenoid paste formulation and the dry formulation were 0.90 and 0.85 mg lutein per 100 gram edible part of egg, respectively. The eggs collected from the control treatment and the ordinary carotenoids formulation treatment showed 0.09 mg and 0.65 mg lutein per 100 gram edible part of the egg, respectively. From these results it can be seen that there is a 38.46% increase in the lutein deposition from the new paste formulation over the ordinary formulation. The lutein increase from the dry formulation over the ordinary formulation was 30.77%. It is also important to note that there is a 10 fold increase in the lutein deposition in the egg from the new paste formulation over the eggs collected from the birds treated with the control diet. The new dry formulation showed a 9.4 fold increase over the control treatment.

Figure 8:
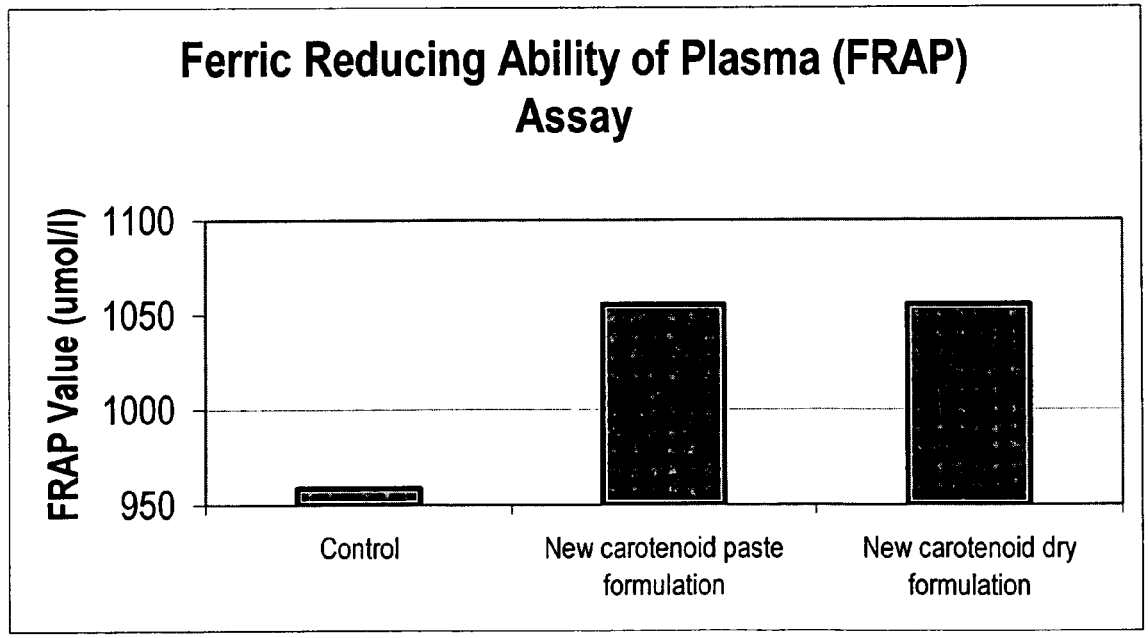
FIG. 8 is a graph showing the effect of new formulation and the new formulation in dry form on the Ferric Reducing Ability of Plasma (FRAP) assay of the chicken blood plasma.

FIG. 8 shows the effect of the new pigment formulation on the immune response of the birds. The FRAP assay technique was employed to measure the antioxidant power of the blood plasma taken from the birds. Potentially harmful reactive oxygen species (ROS) are produced as a consequence of normal aerobic metabolism. These free radicals are usually removed or inactivated in vivo by antioxidants. Antioxidants provide defense mechanism to prevent the generation of ROS. Thus, oxidative stress-induced tissue damage is minimized. A deficiency of antioxidant defense may lead to a situation of increased oxidative stress, and this may lead to variety of disorders. Therefore, presence of antioxidants in the plasma will boost the immune response of the birds and prevent them from diseases. Lutein is a biologically active antioxidant. A biological antioxidant is defined as any substance that when present at low concentrations compared to those of an oxidisable substrate, significantly delays or prevents oxidation of that substrate. However, unless an antioxidant prevents the generation of ROS, for example, by metal chelation or enzyme-catalyzed removal of a potential oxidant, a redox reaction still occurs. The difference is that the oxidizing species reacts with the antioxidant instead of the substrate, i.e. the antioxidant reduces the oxidant. In this context, antioxidant power may be referred to analogously as reducing ability. The FRAP assay method measures ferric reducing ability of plasma containing antioxidant. In this present study the plasma contains lutein as the antioxidant. At low pH when a ferric tripyridlytriazine ($Fe^{III}$-TPTZ) complex is reduced to the ferrous ($Fe^{II}$) form, an intense blue color with an absorption maximum at 593 nm develops. The lutein present in the blood plasma will reduce the Ferric reagent to ferrous state producing the intense blue color. Presence of more lutein is expected to produce more intense blue color. Therefore, the plasma samples taken from birds treated with the control diet and the two new paste and dry formulations were subjected to this FRAP assay and their antioxidant power was measured. The results showed that the new formulations increased the antioxidant power of the birds.

From this example 3 it is evident that the new formulation can be used in the dry form. The efficiency of the new formulation did not affect when the paste form was converted to dry form. From FIG. 6 it can be seen that the lutein deposition was significantly higher for the new paste and dry formulations than the ordinary carotenoid formulation. Results in FIG. 7 shows that the lutein deposition in the eggs was significantly higher for the new formulations than the ordinary carotenoid formulation. FIG. 8 shows the antioxidant power of the blood plasma samples taken from the birds treated with the control and the experimental diets. It is evident from the results that the plasma samples taken from the birds treated with the new formulations showed higher antioxidant power than the plasma samples taken from the birds treated with control diet.

Conclusion

From the present trial it is apparent that the new formulation can be used in the paste form or dry form without compromising the efficiency of the new formulation. The trial results showed that the new formulations showed significantly higher bioavailability for lutein in chicken blood and egg. It is also evident from this study that the new formulations can enhance the antioxidant power of the blood and boost immune response of the birds.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

We claim:

1. A method for preparing a formulation for increasing the bioavailability of carotenoids in poultry, comprising the steps of:
   (a) adding to a reaction vessel a source of a non-saponified carotenoid selected from the group consisting of lutein, zeaxanthin, beta-carotene, trans-capsanthin, capsorubin and the carotenoid derivatives from lycopene;
   (b) adding to the reaction vessel a solvent, and optionally a chelating agent and an antioxidant, to form a composition;
   (c) mixing the composition to substantial homogeneity;
   (d) adding an alkali solution to the composition under mixing;
   (e) incubating the composition at elevated temperature for a time sufficient to saponify the carotenoid; and
   (f) adding vegetable oil and a surfactant to the saponified composition under mixing to form an emulsion.

2. A formulation for increasing the bioavailability of carotenoids in poultry, prepared according to the method of claim 1.

3. A formulation as defined in claim 2, wherein the vegetable oil is selected from the group consisting of corn oil, rapeseed oil, soybean oil, palm oil, sunflower oil and coconut oil.

4. A formulation as defined in claim 2, wherein the chelating agent is selected from the group consisting of EDTA and citric acid.

5. A formulation as defined in claim 2, wherein the antioxidant is selected from the group consisting of ethoxyquin butylated hydroxy anisole, butylated hydroxy toluene, propyl gallate, octyl gallate, gallic acid, catechins, polyphenols, tocopherols, rosemary extract and curcuminoids.

6. A formulation as defined in claim 2, wherein the alkali is selected from the group consisting of potassium hydroxide and sodium hydroxide.

7. A formulation as defined in claim 2, wherein the solvent is selected from the group consisting of propylene glycol and benzyl alcohol.

8. A formulation as defined in claim 2, wherein the carotenoid is between about 0.01 wt % and about 10 wt % of the formulation.

9. A formulation as defined in claim 3, wherein the vegetable oil is between about 1 wt % and about 90 wt % of the formulation; wherein the surfactant is between about 0.001 wt % and about 10 wt % of the formulation; wherein the chelating agent is between about 0.001 wt % and about 1 wt % of the formulation; wherein the antioxidant is between about 1 wt % and about 10 wt % of the formulation; wherein the alkali is between about 1 wt % and about 20 wt % of the formulation; and wherein the solvent is between about 1 wt % and about 20 wt % of the formulation.

10. A formulation as defined in claim 2, further comprising a sufficient amount of a dry carrier to produce a dry, free-flowing product.

11. A formulation as defined in claim 10, wherein the carrier is selected from the group consisting of rice bran, wheat bran, silica, bentonite, calcium carbonate and vermiculite.

12. A method for increasing the deposition of carotenoids in egg yolk produced by birds, comprising the steps of supplementing a diet fed to the birds by adding the formulation of claim 2 to raise the level of carotenoids in the egg yolks to at least 0.80 mg carotenoid per 100 grams of edible portion of the egg.

13. A method for increasing the blood level of carotenoids in birds, comprising the steps of supplementing a diet fed to the birds by adding the formulation of claim 2 to raise the level of carotenoids in the blood to at least 2.0 ppm of the carotenoid.

14. A method for increasing the antioxidant level in the blood of birds, comprising the steps of supplementing a diet fed to the birds by adding the formulation of claim 2 to raise the level of antioxidants in the blood to at least 1 mmol per liter of ferric reducing ability of plasma.

15. A method as described in claim 12, wherein the formulation raises the level of carotenoids in the egg yolks to at least 1.0 mg carotenoid per 100 grams of edible portion of the egg.

16. A method as described in claim 13, wherein the formulation raises the level of carotenoids in the blood to at least 4.0 ppm of the carotenoid.

17. A method for increasing by at least 4-fold the blood level of a carotenoid birds, comprising the step of supplementing the diet fed to the birds with a formulation according to claim 2.

* * * * *